(12) United States Patent
Apolonskiy et al.

(10) Patent No.: US 10,101,268 B2
(45) Date of Patent: Oct. 16, 2018

(54) METHOD AND APPARATUS FOR MEASURING A SPECTRAL SAMPLE RESPONSE

(71) Applicants: Max-Planck-Gesellschaft zur Foerderung der Wissenschaften e.V., Munich (DE); Ludwig-Maximilians-Universitaet Muenchen, Munich (DE)

(72) Inventors: Alexander Apolonskiy, Garching (DE); Ioachim Pupeza, Tuerkenfeld (DE); Ferenc Krausz, Garching (DE); Ernst Fill, Garching (DE)

(73) Assignees: Max-Planck-Gesellschaft zur Foerderung der Wissenschaften e.V., Munich (DE); Ludwig-Maximilians-Universitaet Muenchen, Munich (DE)

( * ) Notice: Subject to any disclaimer, the term of this patent is extended or adjusted under 35 U.S.C. 154(b) by 0 days.

(21) Appl. No.: 15/538,018

(22) PCT Filed: Dec. 18, 2015

(86) PCT No.: PCT/EP2015/002562
§ 371 (c)(1),
(2) Date: Jun. 20, 2017

(87) PCT Pub. No.: WO2016/102056
PCT Pub. Date: Jun. 30, 2016

(65) Prior Publication Data
US 2018/0003623 A1   Jan. 4, 2018

(30) Foreign Application Priority Data

Dec. 23, 2014 (EP) .................... 14004401

(51) Int. Cl.
*G01J 3/00* (2006.01)
*G01N 21/35* (2014.01)
(Continued)

(52) U.S. Cl.
CPC ........... *G01N 21/35* (2013.01); *C07D 231/12* (2013.01); *G01N 21/3586* (2013.01);
(Continued)

(58) Field of Classification Search
CPC ........ G01J 3/00; G01J 3/28; G01J 3/02; G01J 3/44; G01N 21/65
See application file for complete search history.

(56) References Cited

U.S. PATENT DOCUMENTS 5,222,495 A    6/1993  Clarke et al.
5,467,767 A *  11/1995 Alfano ............... A61B 5/0071
                                                    600/476
(Continued)

FOREIGN PATENT DOCUMENTS

EP    0680273 B1    11/1995
WO    2007121598 A1 11/2007
WO    2011117572 A1  9/2011

OTHER PUBLICATIONS

Bernhardt et al. (2010). Mid-infrared dual-comb spectroscopy with 2.4 μm Cr 2+: ZnSe femtosecond lasers. Applied Physics B: Lasers and Optics, 100(1), 3-8.
(Continued)

*Primary Examiner* — Abdullahi Nur
(74) *Attorney, Agent, or Firm* — Caesar Rivise, PC

(57) ABSTRACT

A method of measuring a spectral response of a biological sample (1), comprises the steps generation of probe light having a primary spectrum, irradiation of the sample (1) with the probe light, including an interaction of the probe light and the sample (1), and spectrally resolved detection of
(Continued)

the probe light having a modified spectrum, which deviates from the primary spectrum as a result of the interaction of the probe light and the sample (1), said modified spectrum being characteristic of the spectral response of the sample (1), wherein the probe light comprises probe light pulses (2) being generated with a fs laser source device (10). Furthermore, a spectroscopic measuring apparatus is described, which is configured for measuring a spectral response of a biological sample (1).

22 Claims, 2 Drawing Sheets

(51) Int. Cl.
    *C07D 231/12*     (2006.01)
    *G01N 21/3586*     (2014.01)

(52) U.S. Cl.
    CPC ............... *G01N 2021/3595* (2013.01); *G01N 2201/0697* (2013.01); *G01N 2201/06113* (2013.01); *H05K 999/99* (2013.01)

(56) References Cited

U.S. PATENT DOCUMENTS

| | | |
|---|---|---|
| 6,236,047 B1 | 5/2001 | Malin et al. |
| 7,101,340 B1 | 9/2006 | Braun |
| 7,203,345 B2 | 4/2007 | Rowe et al. |
| 7,403,805 B2 | 7/2008 | Abreu |
| 8,022,366 B2 | 9/2011 | Hartley |
| 2008/0088838 A1* | 4/2008 | Raicu .................... G01J 3/2823 356/318 |
| 2009/0303574 A1* | 12/2009 | Gunter ............... G01N 21/3581 359/328 |
| 2012/0266653 A1 | 10/2012 | Yaniv et al. |
| 2013/0221222 A1 | 8/2013 | Baiz et al. |
| 2015/0097118 A1 | 4/2015 | Zheng et al. |

OTHER PUBLICATIONS

Cao et al. (2006). Breath analysis: potential for clinical diagnosis and exposure assessment. Clinical chemistry, 52(5), 800-811.
De Lacy Costello et al. (2014). A review of the volatiles from the healthy human body. Journal of breath research, 8(1), 014001: 1-29.
Diem et al. (2013). Molecular pathology via IR and Raman spectral imaging. Journal of biophotonics, 6(11-12), 855-886.
Dumas et al. (2007). Adding synchrotron radiation to infrared microspectroscopy: what's new in biomedical applications?. Trends in biotechnology, 25(1), 40-44.
Liu et al. (2013). Mid-infrared time-domain spectroscopy system with carrier-envelope phase stabilization. Applied Physics Letters, 103(18), 181111: 1-5.
Parz et al. (2010). Time-domain spectroscopy of mid-infrared quantum cascade lasers. Semiconductor Science and Technology, 26(1), 014020: 1-6.
Risby et al. (2006). Current status of clinical breath analysis. Applied Physics B: Lasers and Optics, 85(2), 421-426.
Shim et al. (2006). Femtosecond pulse shaping directly in the mid-IR using acousto-optic modulation. Optics letters, 31(6), 838-840.
Sponring et al. (2009). Release of volatile organic compounds from the lung cancer cell line NCI-H2087 in vitro. Anticancer research, 29(1), 419-426.
Znakovskaya et al. (2014). Dual frequency comb spectroscopy with a single laser. Optics letters, 39(19), 5471-5474.
International Search Report from corresponding PCT/EP2015/002562 dated Mar. 21, 2016.
Pupeza et al. (2014). Compact 0.1-W source of octave-spanning mid-infrared femtosecond pulses centered at 10 µm. In Lasers and Electro-Optics (CLEO), 2014 Conference on (pp. 1-2). IEEE.
Johnson et al. (2001). Enhanced depth resolution in terahertz imaging using phase-shift interferometry. Applied Physics Letters, 78(6), 835-837.
Krishnamurthy et al. (2001). Characterization of thin polymer films using terahertz time-domain interferometry. Applied Physics Letters, 79(6), 875-877.
Liu et al. (2007). Sensing minute changes in biological cell monolayers with THz differential time-domain spectroscopy. Biosensors and bioelectronics, 22(6), 1075-1080.
Fattahi et al. (2013). Efficient, octave-spanning difference-frequency generation using few-cycle pulses in simple collinear geometry. Optics Letters, Optical Society of America, 38(20), 4216-4219.
Schliesser et al. (2012). Mid-infrared frequency combs. Nature Photonics, pp. 440-449.
Sell et al. (2008). Phase-locked generation and field-resolved detection of widely tunable terahertz pulses with amplitudes exceeding 100 MV/cm. Optics Letters, Optical Society of America, 33(23), 2767-2769.

\* cited by examiner

METHOD AND APPARATUS FOR MEASURING A SPECTRAL SAMPLE RESPONSE

CROSS-REFERENCE TO RELATED APPLICATIONS

This application is a U.S. National Phase Application of PCT/EP2015/002562, filed Dec. 18, 2015, which claims priority to EP 14004401.7, filed Dec. 23, 2014, the contents of which applications are incorporated herein by reference in their entirety for all purposes.

BACKGROUND OF THE INVENTION

The present invention relates to a method of measuring a spectral response of a biological sample. In particular, the invention relates to a method of measuring the spectral response by irradiating the sample with broadband probe light and sensing spectral changes of the probe light, which result from an interaction of the probe light with the sample, like a method of measuring absorption and/or reflection of the probe light at the sample. Furthermore, the invention relates to a spectroscopic measuring apparatus for measuring a spectral response of a biological sample, in particular including a broadband light source for irradiating the sample with probe light and a detector device for spectrally resolved detecting changes of the probe light resulting from an interaction of the probe light with the sample. Applications of the invention are available in spectroscopy of samples, in particular for analysing a composition and/or condition of a sample. Biological samples, which can be analysed comprise e.g. samples from a human or animal organism or samples taken from a natural environment.

For illustrating background art relating to techniques for analysing substance samples, in particular biological samples for diagnostic purposes, reference is made to the following prior art documents:
[1] B. de Lacy Costello et al., "A review of the volatiles from the healthy human body", J. Breath Res. 8, 014001 (2014);
[2] T. H. Risby et al., "Current status of clinical breath analysis", Appl. Phys. B 85, 421-426 (2006);
[3] W. Cao et al., "Breath analysis: Potential for clinical diagnosis and exposure assessment", Clinical Chemistry 52, 800-811 (2006);
[4] US 2012/0266653 A1;
[5] U.S. Pat. No. 7,101,340 B1;
[6] WO 2011/117572 A1;
[7] U.S. Pat. No. 5,222,495;
[8] U.S. Pat. No. 8,022,366 B2;
[9] U.S. Pat. No. 6,236,047 B1;
[10] U.S. Pat. No. 7,403,805 B2;
[11] U.S. Pat. Non. 7,203,345 B2;
[12] EP 0,680,273 B1;
[13] P. Dumas et al., "Adding synchrotron radiation to infrared microspectroscopy: what's new in biomedical applications?" TRENDS in Biotechnology 25, 40 (2006);
[14] I. Znakovskaya et al., "Dual frequency comb spectroscopy with a single laser", Opt. Lett. 39, 5471 (2014);
[15] A. Sponring et al., "Release of volatile organic compounds from the lung cancer cell line NCI-H2087 In Vitro", Anticancer Research 29, 419 (2009);
[16] M. Diem et al., "Molecular pathology via IR and Raman spectral imaging", J. Biophoton. 6, 855 (2013);
[17] W. Parz et al., "Time-domain spectroscopy of mid-infrared quantum cascade lasers", Semicond. Sci. Technol. 26 (2011) 014020;
[18] WO 2007/121598 A1;
[19] US 2013/0221222 A1;
[20] B. Bernhardt et al., "Mid-infrared dual-comb spectroscopy with 2.4 μm Cr2+:ZnSe femtosecond lasers", Appl. Phys. B (2010) 3; and
[21] Sh. Liu et al., "Mid-infrared time-domain spectroscopy system with carrier-envelope phase stabilization", Appl. Phys. Lett. 103, 181111 (2013).

In medicine there is an urgent need for a minimally invasive, rapid, reliable, and cost-effective diagnosis of diseases at early stages (screening) and for monitoring their response to therapy. It is generally known that the analysis of biological samples, including body fluids and gases emitted from the body is well suited for this purpose because they contain a multitude of compounds characteristic of the health status of a person. About 1760 different such components are known, specifically 874 in exhaled breath, 504 in skin emanations, 279 in urine headspace, 130 in blood, 381 in feces and 353 in saliva [1]. Importantly, some compounds exist only in the liquid phase some in both gas and liquid phases. In particular, breath aerosol is potentially rich of heavy compounds.

Any change in the structure of molecular constituents of a human cell invariably causes a change in the mid-infrared (MIR) absorption spectrum of the cell itself or of its metabolic emanations. As a consequence, small modifications in the spectrum offer a means of early detection and diagnosis of many diseases. The statistically-proven spectral traces of a disease will provide reliable "fingerprint" information for its early diagnosis.

In classical diagnostics, the compounds of biologicals samples are detected by chemical analysis or by gas chromatography combined with mass spectrometry [2, 3]. However, these methods i) do not allow for fast analysis, ii) can modify or even destroy some compounds and iii) are blind for conformational changes in the structure of DNA, which may, without any change in mass, initiate severe diseases.

Furthermore, a number of spectroscopic methods have been suggested for the examination of body fluids and gases [4-12, 16]. In [4] gas analysis alone is proposed whereas actually all phases (gas, liquid, solid, aerosol) can contribute to diagnostic knowledge. In [5] spectral analysis of breath by cw lasers is suggested and thus the number of available spectral data points and their informative value is very limited. In [6] a narrow range of wavelengths is used and only three gases are detected, restricting the range of diagnostics to diabetes.

Further conventional approaches dealing with the spectral analysis of body liquids, such as blood or saliva, are described in [7] and [8]. Patent [7] proposes non-invasive blood analysis by comparing the absorption of two closely spaced wavelengths in blood. In [8] a compact MIR spectrometer is proposed for measuring blood sugar (glucose) and other blood and body fluid analytes. It consists of a modulated thermal emitter and a low-resolution spectrometer containing quarter wave plates acting as interference filters.

Diffusively reflected radiation of bands in the range of 1100 to 5000 nm is used in [9] to determine concentrations of blood analytes by chemometric techniques. Another technique uses a contact device placed on the eye to investigate spectral changes in the conjunctiva and the tear film [10]. Thermal radiation from the eye itself or external radiation supplied by a fiber are employed for this purpose. Spectroscopy is used in [11] to identify individuals by analysing the reflection of near-infrared radiation from human tissue. In [12] a catheter containing a fiberoptic bundle is inserted into gastro-intestinal compartments for the detection of fluorescence and absorption of light by their contents.

As a general disadvantage, none of the conventional methods is capable of providing the full information on the health status of a person that would in principle be available. The conventional techniques are specialized for using a single phase for diagnosis only. Furthermore, they employ only a narrow spectral range within the full MIR-bandwidth, and they are not sensitive enough to detect subtle changes in the spectrum indicative of a disease. In other words, the known approaches offer access only to a small fraction of the full Molecular fingerprint and even that with a sensitivity and signal-to-noise ratio that is insufficient for reliable identification and diagnosis of diseases.

Recently the use of synchrotron radiation has been explored for spectroscopic imaging of cells with various kinds of disorders [13]. This radiation is broadband and about two orders of magnitude more intense than that of a thermal source. However, the application of synchrotrons for routine diagnostics and for screening a large number of patients does not appear practical.

The above limitations do not occur with analysing biological samples for diagnostic purposes only. Other spectroscopic investigations, e. g. of environmental samples or laser media, have similar disadvantages, in particular in terms of sensitivity, selectivity and limited use of available information.

As an example, [17] discloses a spectroscopic investigation of a quantum-cascade-laser (QCL). For measuring gain and absorption, the QCL is irradiated with 10 fs laser pulses having a wavelength in the MIR range, and the spectroscopic response of the QCL is investigated using a time domain spectroscopy setup with electro-optic detection. The application of the conventional method is restricted to the investigation of strong absorbing QCL materials. Due to the use of a Ti-sapphire laser, the laser pulses have a low intensity, so that measurements of weak absorptions are excluded. Furthermore, the laser pulses have a narrowband characteristic, resulting in limitations for investigating other materials with spectral features in a broad wavelength range.

Another application of a Ti-sapphire laser for creating THz radiation in a range of 1.3 to 4.8 THz, corresponding to a wavelength in a range of 62 μm to 230 μm, by optical rectification in an organic material is disclosed in [18]. According to [19], a narrow frequency range around 6 μm is investigated using a Ti-sapphire laser. Due to the narrow wavelength ranges, the low radiation intensity and a limited stability of the laser setup, these conventional technique are not suitable for an efficient spectral broadband characterization of materials.

Dual-comb spectroscopy for investigating a gas sample is described in [20]. This method is restricted to an FTIR measurement in a narrow wavelength range between 2.3 μm and 2.6 μm, reaching only a low sensitivity in a ppm-range. Again, this technique is not suitable for investigating materials with spectral features in a broad wavelength range.

MIR-radiation in a range from 8 μm to 12 μm can be created on the basis of Er:fibre laser emissions at three wavelengths of 1050 nm, 1350 nm and 1550 nm as disclosed in [21]. This technique requires a complex loop control, resulting in restricted applicability of the MIR-radiation.

A first objective of the invention is to provide an improved method of measuring a spectral response of a sample, which is capable of avoiding limitations or disadvantages of conventional techniques. In particular, it is the first objective of the invention to provide the measuring method with an increased sensitivity, improved signal-to-noise-ratio (SNR), enhanced selectivity and/or improved capability of covering an extended spectral range, e. g. in the mid-infrared spectral range (MIR). A second objective of the invention is to provide an improved spectroscopic measuring apparatus, which is adapted for measuring a spectral response of a sample to a probe light irradiation, wherein the spectroscopic measuring apparatus is capable of avoiding limitations and disadvantages of conventional techniques. In particular, the spectroscopic measuring apparatus is to be capable of providing improvements in terms of sensitivity, SNR, selectivity and/or broadband coverage.

These objectives are correspondingly solved by a spectral response measuring method and a spectroscopic measuring apparatus of the invention.

BRIEF SUMMARY OF THE INVENTION

According to first general aspect of the invention, the above objective is solved by a method of measuring a spectral response of a biological sample, wherein probe light pulses (pulses of electromagnetic radiation) are generated with a fs (femtosecond) laser source device, directed onto the sample to be investigated and detected after an interaction with the sample. The probe light pulses provide probe light having a primary spectrum, which is formed by the frequency components of the probe light pulses. The term "primary spectrum" refers to the spectral composition of the probe light pulses before an interaction with the sample. Due to the creation of the probe light pulses with an fs laser source device, the primary spectrum is a continuous or quasi-continuous spectrum, the shape of which is determined by the output of the fs laser source device, e. g. by the specific oscillator and/or amplifier process, optionally combined with DFG and/or pulse compressing, implemented by the fs laser source device.

Due to the generation of the probe light pulses with the fs laser source device, the primary spectrum is a broadband spectrum, which covers a spectral range including a plurality of spectral bands (spectral response features) of interest. Due to the interaction with the sample, the probe light pulses get a modified spectrum, which deviates from the primary spectrum. The term "modified spectrum" refers to the spectral composition of the probe light pulses after the interaction with the sample. The modified spectrum comprises a spectral shape of the primary spectrum being changed by at least one spectral band (spectral line) of a component included in the sample. Preferably, the modified spectrum includes a plurality of spectral bands of one or multiple component(s) included in the sample. By spectrally resolved detection of the probe light after the interaction with the sample, all spectral bands of the at least one component can be sensed. The modified spectrum, in particular the difference between the modified spectrum and the primary spectrum, preferably the positions, relative amplitudes and/or spectral phases of spectral bands created by the sample, is characteristic of the spectral response of the sample.

According to a second general aspect of the invention, the above objective is solved by a spectroscopic measuring apparatus (spectrometer), which is adapted for measuring a spectral response of a biological sample, wherein the spectroscopic measuring apparatus comprises a probe light source for irradiating the sample under investigation with probe light having a primary spectrum and a detector device for a spectrally resolved detection of the probe light pulses after an interaction with the sample. According to the invention, the probe light source comprises an fs laser source device, which is configured for generating fs probe light pulses.

Advantageously, the above objectives are solved by providing the fs laser source device, which combines the following key features of the invention. Firstly, the use of the fs probe pulses provides a broadband radiation covering the entire spectral range of interest, in particular in case of investigating biological samples, e. g. for diagnostic purposes. The fs probe pulses have a primary spectrum covering a spectral range, which allows the excitation of vibrational and/or rotational transitions in sample components, in particular organic molecules included in the sample. Due to the broadband spectrum of the fs probe pulses, the spectral response of the sample can be detected like a specific spectral band pattern (spectral "fingerprint"). The spectral response is specific for sample components in terms of the spectral positions of spectral bands in the spectral band pattern and the relative intensities of the spectral bands. Secondly, compared with conventional techniques, the fs laser source device provides the probe light pulses with high power and an ultrashort-pulsed temporal structure of the radiation, permitting a detection of narrow spectral bands (constituents of the molecular fingerprint) with unparalleled sensitivity. The power of the fs probe light pulses is increased compared with the power of thermal broadband sources and synchrotron sources by at least 4 and 2 orders of magnitude, respectively. In particular, the increased probe light pulse power and ultrashort pulse duration allow a detection of the spectral response with essentially reduced SNR compared with conventional techniques. Thirdly, the use of the fs laser source device allows the application of rapid spectroscopic techniques for detecting the modified spectrum of the probe light. The speed of analysis can be essentially increased, which is an advantage in particular in the field of investigating biological samples. Furthermore, the ease of operation makes the use of the inventive technique manageable under practical conditions, e. g. with the diagnostic application of the invention even in hospitals or doctor's practices.

With preferred embodiments of the invention, which can be implemented in combination or sub-combination, the probe light pulses have at least one of the following pulse characteristics. According to a first preferred variant, the pulse duration of the probe light pulses is below a reciprocal frequency width of a spectrum spanned by spectral response features, in particular one or multiple spectral bands, occurring in the spectrum of the sample, i.e. in the modified spectrum of the probe light. Due to this relationship, detecting the probe light with a time-domain-metrology technique is facilitated. If the spectrally resolved detection of the probe light with the modified spectrum is based on a temporal sampling of the time structure of the probe light pulses after the interaction with the sample, trails of the spectral response features can be detected with improved SNR, preferably even with a noise-free background, if they occur in a time range after the pulse duration of the probe light pulses.

With a further preferred variant, the fs probe light pulses have pulse duration equal to or below 100 fs, preferably 50 fs, particularly preferred equal to or below 20 fs, e. g. 10 fs. Advantageously, with these pulse durations, a broadband probe light is created. Furthermore, the spectral response features of typical samples under investigation influence the time structure of the probe light pulses in a time range outside of the probe light pulse duration only.

Furthermore, the average power of the probe light pulses can be increased by shortening the near infrared (NIR) driving pulse duration. Thus, with a preferred further variant of the invention, the probe light pulses preferably are created with an average power above 50 mW, particularly preferred above 500 mW, e. g. up to 5 W.

The short pulse duration of the probe light pulses further influences a spectral bandwidth of the primary spectrum. Thus, with a further preferred variant of the invention, the primary spectrum has the spectral bandwidth covering at least one frequency octave, particularly preferred at least two frequency octaves. Accordingly, the detection of a specific molecular fingerprint of the sample is facilitated.

Preferably, the spectral bandwidth covers a mid-infrared (MIR) range. With particularly preferred embodiments of the invention, the primary spectrum covers a wavelength range including wavelengths of at least 5 µm, particularly preferred at least 3 µm and/or at most 15 µm, particularly preferred at most 30 µm. These wavelength ranges correspond to frequency ranges covering the spectral response features of samples under investigation. In particular the MIR wavelength range laser spectroscopy of 3 µm to 10 µm, 3 µm to 20 µm or 3 µm to 30 µm offers advantages for a quantitative detection of smallest concentrations of components due to the high radiative power and the strong vibrational/rotational absorption bands of organic molecules.

As a further advantage of the invention, the fs laser source device may comprise any available laser source setup, which is capable of providing the fs probe light pulses with a power and spectral and temporal features selected in dependency on the particular application of the invention, preferably with at least one of the above pulse characteristics. According to a preferred embodiment of the invention, the fs laser source device comprises a combination of a driving source creating driving pulses (fundamental wave) and a difference frequency generation (DFG) unit which is adapted for creating the probe light pulses by intra-pulse frequency differences of the driving pulses.

The driving source is a laser source emitting the driving pulses with durations e. g. below 1 ps, preferably below 500 fs. The driving pulses include frequency components which are subjected to the intra-pulse-DFG resulting in an extended number of frequency components in a spectral range with reduced frequencies (increased wavelengths) compared with the driving pulses. The power of the DFG output is proportional to the squared input intensity of the driving pulses. As an essential advantage of generating the probe light pulses by DFG, the temporal structure of the probe light pulses is improved over the temporal structure of the driving pulses. Satellite peaks eventually occurring in the temporal structure of the driving pulses are suppressed by the non-linear DFG process. The satellite-free temporal structure of the probe light pulses has particular advantages for reducing the SNR in the detection of the spectral sample response. Optionally, the fs probe light pulses created with the fs laser source device, e. g. with the combination of the driving source and the DFG unit, can be subjected to a further pulse cleaning technique for suppressing residual satellites in the time structure. Furthermore a DFG process can be used, which includes recycling of the fundamental pulses in an enhancement cavity, thus resulting in several-watt coherent broadband MIR radiation probe light pulses, surpassing the performance of state-of-the-art MIR sources by order of magnitude.

Advantageously, multiple driving sources are available, which can be included in the fs laser source device. Preferably, the driving source includes one of a fiber laser and a disk laser, e. g. an Yb-YAG disk laser or a Ho-YAG disk laser. These types have advantages in terms of providing drive pulses with a high power and repetition rate. As an example, the Yb-YAG disk laser is a laser oscillator including an Yb-YAG disk creating the driving pulses by Kerr lens mode locking with a centre wavelength of 1030 nm, a repetition rate of 100 MHz and a pulse duration of 300 fs, allowing the creation of the probe light pulses with a pulse duration below 20 fs and a spectral width from 5 µm to 15 µm. As a further alternative, the fs laser source device may comprise another oscillator-amplifier combination, like e. g. a MOPA (master oscillator power amplifier) laser system creating the probe light pulses by optical parametric generation in a nonlinear crystal.

A driving source emitting driving pulses with an centre wavelength equal to or above 2 µm, in particular the Kerr lens mode locked Ho-YAG disk laser, has particular advantages in terms of increasing the bandwidth and average power of the probe light pulses. Compared with e. g. the Yb-YAG disk laser, the photon energy is reduced, thus decreasing a risk of unintended 2-photon-absorptions in the DFG unit. Accordingly, a thickness of the optically nonlinear crystal of the DFG unit can be reduced so that an increased bandwidth is available for the phase matching of the DFG process. In particular, using driving pulses with the average wavelength equal to or above 2 µm allows the provision of a DFG crystal in the DFG unit having a thickness such that the probe light pulses created by the DFG process have a bandwidth in a range of 3 µm to 30 µm.

The term "spectral response" refers to any response of the sample to the irradiation with the probe light pulses, which results in a spectral change of the probe light pulses. Advantageously, different types of spectral responses can be sensed, which can be selected in dependency on the available measuring geometry and/or the condition of the sample. With preferred applications of the invention, the spectral response comprises at least one of an absorption spectrum and a reflection spectrum of the sample. Preferably, the absorption spectrum is collected with transparent samples, like e. g. a transparent liquid, while the reflection spectrum is preferably collected with solid, non-transparent samples. Optionally, both of the absorption and reflection spectra can be measured by adapting the detection geometry. The temporal features of the probe light pulses are not influenced by the interaction with the sample.

The invention is not restricted to a certain physical condition of the sample. According to preferred applications of the invention, the sample may comprise at least one of a solid, like e. g. a biological cell, a cell group or cell culture, or tissue of an organism, a liquid, like e. g. blood or other body liquids, optionally diluted, an aerosol, like e. g. breath including traces of liquid droplets, a gas and a vapour, e. g. emanating from a biological organism. Due to the high sensitivity of the inventive method, spectral responses can be measured even with extremely diluted samples, like the aerosol, gas or vapour, and/or extremely small samples, like a single biological cell.

Preferably, the spectroscopic measuring apparatus includes a sample holder device, which is configured for accommodating the sample. The sample holder device has a shape and structure, which is selected in dependency on the condition of the sample to be investigated. With preferred examples, a sample holder device for accommodating a solid or liquid sample may comprise a cuvette as it is used with conventional spectroscopic measurements. If the interaction of the probe light pulses with the sample is weak, like e. g. with gas-phase samples or diluted liquids, multiple passes of the probe light pulses through the sample may be required to improve the SNR. This can be obtained by providing the sample in a multipass cell. The multipass cell may be included into the beam path to significantly improve the SNR. As an alternative possible improvement, the sample can be arranged in an enhancement cavity. The enhancement cavity can provide a large path length with a significantly smaller volume, substantially improving the effective collection of relevant gas samples. On the other hand, in the condensed phase, the density of absorbing species is many orders of magnitude higher. As a consequence, the absorption length is short, typically a fraction of a millimetre. In this case, the sample holding device is configured for accommodating a layer-shaped sample, which preferably has a thickness equal to or below 1 mm, e.g. in a layer-shaped cuvette with a layer thickness below 50 µm, in particular below 20 µm. The solid or liquid sample can be prepared in form of a large-aperture sub-mm thin sheet deposited on a thin IR-transmitting substrate (in case of a solid sample) or sandwiched between two IR-transmitting substrates (in case of liquid samples, such as blood or saliva). With a further alternative, the sample holding device can be adapted for a total reflection of the probe light so that the interaction of an evanescent wave with the sample is obtained.

The transverse size of the illuminated sample volume can be selected for maximizing the SNR, in particular in condensed-phase samples: Substances indicative of a disease are typically present at very low average concentrations. However, their concentration may be appreciable in affected cells. As a consequence, SNR may be dramatically enhanced by tightly focusing the probe light pulse beam to approach the size of the cells indicative of the disease (indicators) and scanning the laser beam across the aperture of the sample. In this way, the ratio of the number of indicator(s) to that of healthy cells in the illuminated sample volume is maximized and so is the SNR.

It is noted that the sample holder device is not strictly necessary for implementing the invention. The sample may be included in an organism or technical process or environmental condition during the inventive measuring the spectral response of the sample. In particular, the spectral response of cells or tissue can be detected by irradiating a part of the organism directly, e. g. the skin or breath, and by detecting the spectral response in absorption or reflection.

Various spectroscopic techniques may be used for spectrally resolved detecting the probe light pulses after the interaction with the sample. A detector device may comprise a combination of a dispersive element, like e. g. a monochromator, and a sensor being arranged for a serial collection of the spectral response data, while detection with a parallel collection of the spectral response data is preferred. A standard approach is e. g. Fourier-transform infrared spectroscopy (FTIR) as it is widely used for acquiring molecular absorption spectra. Combined with balanced detection and implemented with a dual frequency comb (available from a single laser source, see Ref. [14]), it allows a rapid measurement of small changes in the amplitude of the spectral components of the broadband probe light pulses transmitted through the sample or reflected by the sample.

According to a preferred embodiment of the invention, the detection step comprises time-domain sampling of the probe light pulses for obtaining the temporal shape thereof, combined with a Fourier-transformation of the temporal shape. Advantageously, the Fourier-transform of the temporal shape of the probe light pulses directly provides the spectral response of the sample. Time-domain sampling does not provide only the amplitudes of the spectral components in the spectral response of the sample, but also phase information on the spectral components. This phase information carries important complementary information about the spectral response, e. g. the absorption characteristic of the sample. The time-domain sampling comprises e. g. electro-optic sampling (EOS) of the probe light pulses. EOS spectroscopy provides direct time-resolved access to the electric field waveform of the MIR probe pulse transmitted through or reflected by the sample, yielding—upon Fourier transformation—both the amplitude and the phase of the spectral change caused by resonant absorption in the transmitted or reflected signal.

As an additional advantage, the time-domain sampling provides a background-free measurement of the spectral response. In the time domain, a narrow absorption line of a molecular transition induces a long wave trailing the main pulse in the transmitted signal. This trail contains all (both amplitude and phase) information about the absorption line and can be measured against zero background, thanks (i) to its complete temporal separation from the input radiation (probe light pulse) confined to a minute fraction of the length/duration of that of the absorption-induced trailing signal and (ii) the time-resolved detection in time-domain sampling, in particular EOS.

According to a particularly preferred application of the invention, the sample to be investigated comprises a biological sample from a human or animal organism. The spectral response of the sample is measured for obtaining diagnostically relevant information on the organism. The term "diagnostically relevant information" refers to any information on the sample, in particular the composition thereof, differences compared with reference samples or temporal changes of the sample, which can be used for providing or validating a medical diagnosis. Accordingly, with a preferred embodiment of the invention, the measuring method includes the step of evaluating the spectral response of the sample in order to obtain the diagnostically relevant information. In terms of device features, a preferred embodiment of the spectroscopic measuring apparatus preferably includes a calculation device, which is adapted for processing the spectral response and providing the diagnostically relevant information. Advantageously, the diagnostically relevant information can be output to a user of the inventive technique, e. g. a doctor. Subsequently, the user can provide a diagnosis in consideration of the diagnostically relevant information.

The application of the invention in diagnostics has the following particular advantages. The invention allows for determining spectral traces of diseases in all possible sample phases: gas, liquid, solid and aerosol. The inventors have found that, in contrast to conventional techniques, the invention is capable of accessing the entire molecular fingerprint of compounds indicative of a disease, thus providing a universally applicable technique capable of examining all gases, fluids and solids related to the health status of the body. Implemented with a femtosecond laser, it can provide heating or ablation (nails, hair, skin, blood, urine etc.) of the sample, to allow measurements in the gas phase, where smallest modifications in line intensity or position due to changes in molecular structure can be detected. As a prominent application example, volatile organic compounds released by cancerous cells contained in blood (e. g. by an apparatus similar to that described in [15]) can be analysed and utilized for early cancer detection by the invention. Thanks to its high speed, the invention permits time-dependent measurements on short time scales, important when compounds are released at different instants of time. The fast operation of the spectrometer can also be beneficial for rapid evaporative spectrometry during surgery ([16]).

Being entirely free from any risk, this diagnostic approach—once validated—is ideally suited for early (i.e. frequent) screening of various chronic diseases. Thanks to its non-invasive nature it will facilitate continuous monitoring of a therapy, providing vital information about its efficacy. The method can significantly decrease time and effort expended for medical diagnosis, as well as reduce the inconvenience for patients. It is applicable to a broad range of illnesses e. g. lung diseases, various kinds of cancer, kidney malfunction and metabolic disorder. The speed, convenience and comparatively low cost of the diagnostic technique proposed in this invention makes it suitable for routine examination of a great number of people and thus may improve the health status of a whole population. It is not necessary to chemically analyse single substances in the sample, if the spectral response is sufficient to identify the presence thereof based on the specific fingerprint.

Advantageously, the spectral response evaluation may include various measures, which can be implemented separately or in combination. According to a first variant, diagnostically relevant substances can be identified on the basis of specific spectral bands (location, amplitudes and/or phases) occurring in the modified spectrum. To this end, the calculation device may include a filter unit being adapted for analysing the occurrence and features of the specific bands in the modified spectrum.

According to a further variant, the evaluation step may include a step of comparing at least a portion of the modified spectrum with a stored sample response previously collected with another sample of the same subject under investigation. In other words, a time series of modified spectra can be collected, and the diagnostically relevant information can be obtained by identifying specific changes in the time series of the modified spectra. For this purpose, the calculation unit may include a first comparing unit, which is adapted for comparing at least a portion of the modified spectrum currently detected with at least one stored sample response previously detected.

According to yet another variant, the evaluation step may include a step of comparing at least a portion of the modified spectrum with reference data of other subjects. The other subjects may comprise e. g. healthy or non-healthy organisms, and the reference data may represent spectral response features of a healthy or a sick condition, respectively. Accordingly, the calculation unit may include a second comparing unit, which is adapted for comparing at least a portion of the modified spectrum currently detected with the reference data. In particular, measurements can be performed on a large number of samples extracted from patients and compared to corresponding data acquired from a collection of healthy people. Statistically significant deviations between the two groups will permit establishing reliable indicators of the disease under scrutiny. Careful statistical analysis of the patients sample, e. g. using principal components analysis (PCA), will then allow determination a diagnostically relevant information on his/her condition in a short period of time.

Particularly preferred features of the invention can be summarized as follows. The (a) generation of a femtosecond multi-octave MIR continuum covering the entire molecular fingerprint region of 3 μm to 30 μm at a power level that will exceed that of MIR synchrotron sources by several orders of magnitude and (b) its use for background-free measurement of the complete absorption-induced signal (incl. amplitude and phase information) with a sensitivity and signal-to-noise exceeding—thanks also to the use of low-noise detectors measuring the VIS/NIR sampling signal—that of state-of-the-art FTIR spectrometers by orders of magnitude constitute the key innovations offered by the invention. Advantageously, the invention can be combined with the established techniques for noise suppression and rapid data acquisition (such as balanced detection and dual-comb illumination, respectively) will improve recording of complete vibrational molecular fingerprints for the first time in a single measurement.

BRIEF DESCRIPTION OF SEVERAL VIEWS OF THE DRAWINGS

Further advantages and details of the invention are described in the following with reference to the attached drawings, which show in.

DETAILED DESCRIPTION OF PREFERRED EMBODIMENTS

Preferred embodiments of the invention are described in the following with exemplary reference to particular examples of fs laser source devices and the application of electro-optic sampling. It is emphasized that the invention is not restricted to the described embodiments. In particular, the fs laser source device can be modified for providing the probe light pulses as specified in the present description. Furthermore, the EOS method can be replaced by another spectroscopic technique, like e. g. FTIR spectroscopy. Exemplary reference is made to the preferred application of the invention for providing diagnostically relevant information. It is emphasized that the invention is not restricted to the investigation of biological samples, but rather can be implemented with other samples, like e. g. environmental samples.

Figure 1:
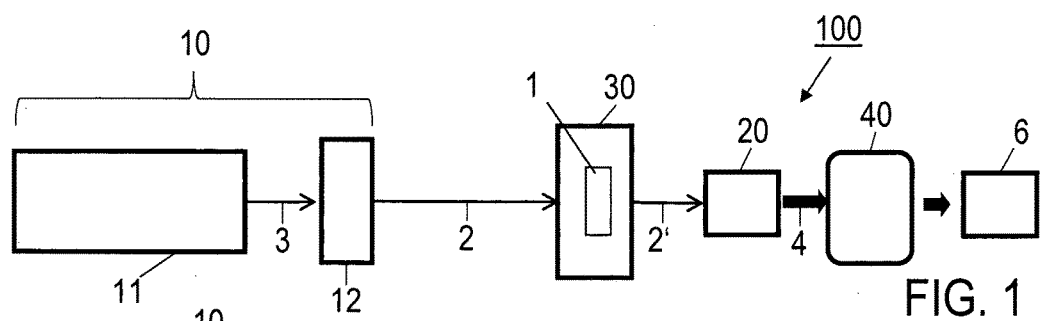
FIG. 1: a first embodiment of a spectroscopic measurement apparatus according to the invention.

FIG. 1 schematically illustrates a first embodiment of the spectroscopic measuring apparatus 100 according to the invention, which comprises the fs laser source device 10, the sample holder device 30, the detector device 20 and a calculation device 40. The fs laser source device 10 includes a driving source 11, like e. g. an Yb-YAG-disk laser resonator combined with a fiber broadening stage and a chirped mirror compressor, and a DFG unit 12. The driving source 11 creates driving pulses 3, e. g. with a centre wavelength 1030 nm, a pulse duration 300 fs and a repetition rate 100 MHz. The DFG unit 12 includes an optically non-linear crystal, like e. g. a LiGaS-based crystal, which is arranged for intra-pulse difference frequency generation. Probe light pulses 2 are output at the DFG unit 12, which have a primary spectrum formed by frequency components according to difference frequencies between intra-pulse frequency components of the driving pulses 3. With the described example, the probe light pulses 2 have a primary spectrum ranging from 3 μm to 30 μm.

The sample holding device 30 accommodates the sample 1 to be investigated. With preferred examples, the sample holding device comprises a single- or multi-pass cuvette accommodating the sample 1. The sample holding device 30 may comprise a sample holder as is known from conventional spectroscopic techniques, including a sample supply and/or tempering devices.

The detector device 20 generally comprises a near-infrared detector, which is configured for a spectrally resolved sensing the probe light pulses 2' having a modified spectrum due to the interaction of the probe light pulses 2 with the sample 1. Preferably, the detector device 20 is adapted for a parallel collection of the spectral response data using e. g. the FTIR- or EOS-technique (see FIG. 2).

The calculation device 40 generally comprises a microcomputer-based control with a calculation unit and optional filtering and/or comparing units. Furthermore, the calculation device 40 may include a data base with reference data from healthy or non-healthy reference subjects. The spectral response 4 as detected with the detector device 20 is evaluated with the calculation device 40 for providing diagnostically relevant information 6, e. g. an information on the presence or non-presence of predetermined substances in the sample 1.

Figure 2:
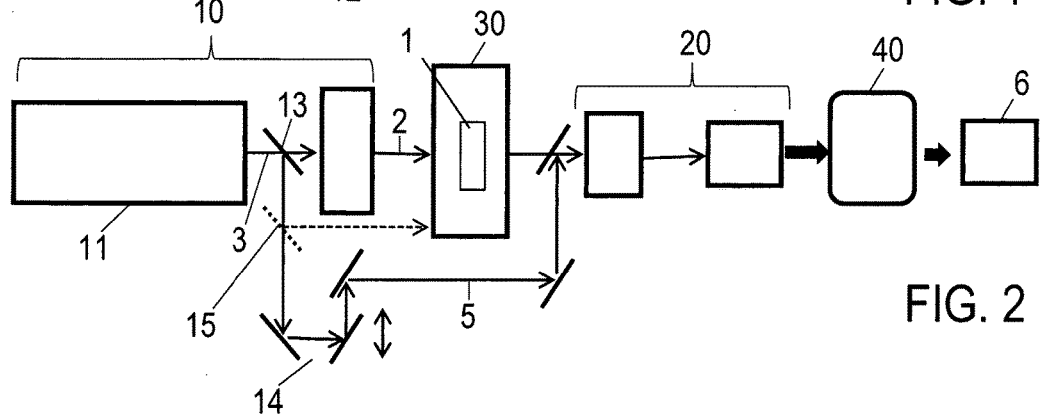
FIG. 2: features of further embodiments of the spectroscopic measurement apparatus according to the invention.

FIG. 2 schematically illustrates further features of preferred embodiments of the inventive spectroscopic measuring apparatus 100, which comprises the fs laser source device 10, the sample holding device 30, the detector device 20, and the calculation device 40. The embodiment of FIG. 2 is adapted for electro-optic sampling the temporal shape of the probe light pulses 2' after the interaction with the sample 1. To this end, the fs laser source device 10 includes a semi-transparent beam splitter element 13, like e. g. a semi-transparent beam splitting mirror, which directs a part of the driving pulses 3 as sampling pulses 5 via a delay line 14 to the detector device 20. The detector device 20 is configured for electro-optic sampling the temporal shape of the probe light pulses 2' using the sampling pulses 5 (see FIG. 3).

Optionally, another beam splitter element 15, like e. g. a semi-transparent beam splitting mirror, can be provided, which directs a part of the driving pulses 3 to the sample 1, as shown with dotted lines in FIG. 2. This part of the driving pulses 3 can be used for pulsed heating a liquid or solid sample so that sample substance is ablated and converted to the vapour phase, which is irradiated with the probe light pulses 3. This ablation technique can be provided with samples taken from an organism, i. e. outside the organism.

Figure 3:
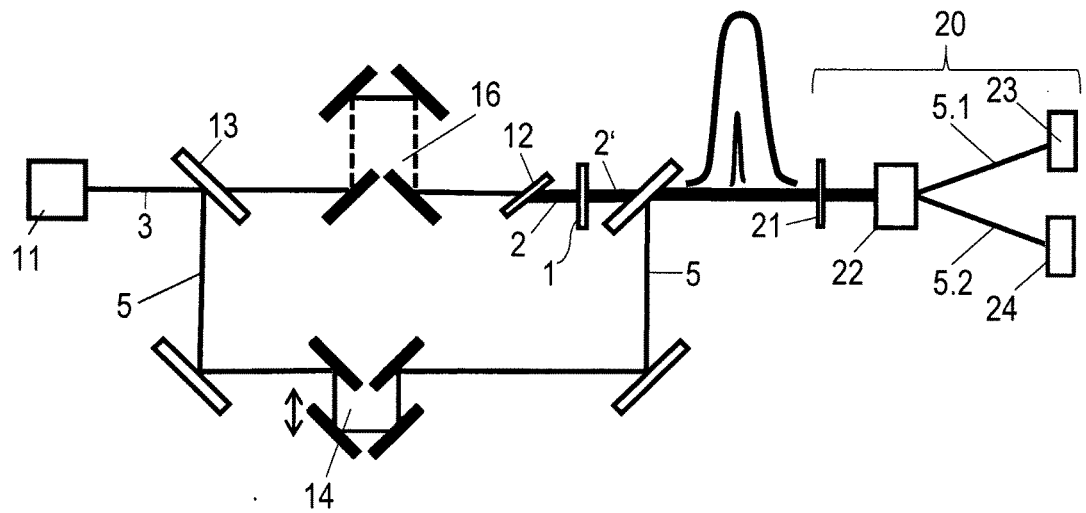
FIG. 3: a schematic illustration of electro-optic sampling used for sensing the spectral response of the sample.

FIG. 3 illustrates further details of electro-optic sampling the temporal shape of the probe light pulses 2'. The NIR driving pulses 3 generated with the driving source 11 are split into two parts. The main part (>90% of the power) is deflected via a fixed delay line 16 to the DFG unit 12. The fixed delay line 16 is arranged for compensating the increased beam path length of the sampling pulses 5. With the DFG unit 12, the driving pulses 3 are converted to the probe light pulses 2 with broadband mid-infrared (MIR) characteristic. The probe light pulses 2 pass the absorbing sample 1, and then they are directed towards an electro-optic crystal 21 of the detector device 20. The electro-optic crystal 21 is an optically non-linear crystal, e. g. GaSe having a $\chi^2$ non-linearity.

The other part of the driving pulses 3 is directed as the sampling pulses 5 via a moveable delay line 14 to the electro-optical crystal 21. The probe light pulses 2' with the modified spectrum and the sampling pulses 5 are superimposed at the electro-optic crystal 21 with varying time delay.

The polarization state of the sampling pulses 5 passing the electro-optic crystal 21 is changed by the electric field of the probe light pulses 2'. By changing the delay between the two pulses with a delay drive unit (not shown), the probe light pulses 2' are sampled at the electro-optic crystal 21. The sampling pulses 5 with the modified polarization state pass a Wollaston prism 22 separating sub-pulses 5.1 and 5.2 with two orthogonally polarized polarization components of the sampling pulses 5. The sub-pulses 5.1 and 5.2 carrying the different polarization components are sensed with detector elements 23 and 24, comprising e. g. photodiodes. The detector elements 23 and 24 are balanced, i. e. calibrated such that a difference between the detector signals of the detector elements 23 and 24 is proportional to the electric field of the probe light pulse 2'. Accordingly, with changing the mutual delay using the moveable delay line 14, the detector signal difference directly provides the temporal shape of the probe light pulses 2'.

Figure 4:
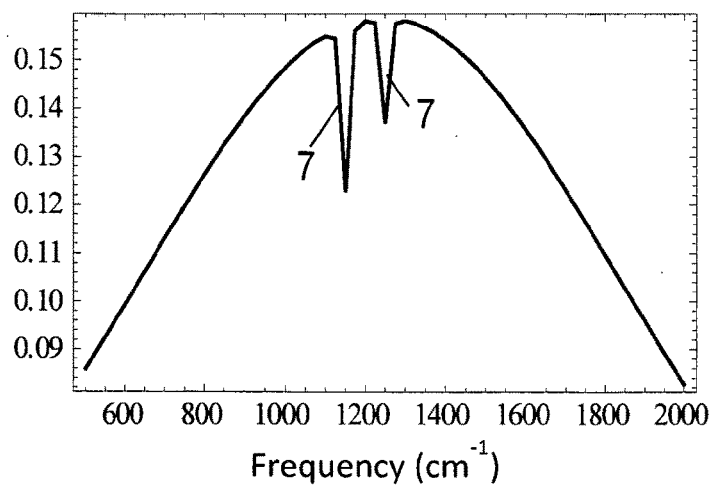
FIG. 4: a schematic illustration of a modified probe light pulse spectrum including spectral bands of a sample.
Figure 5:
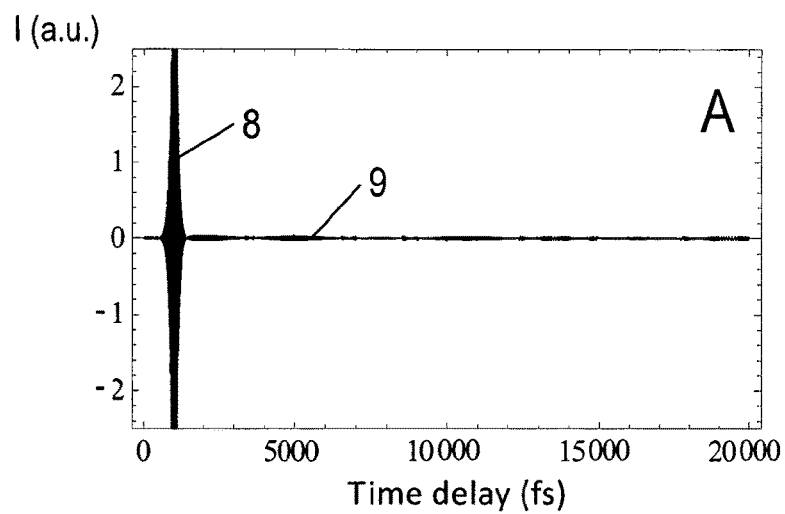
FIG. 5: illustrations of the background-free sensing temporal trails for detecting the spectral response of the sample.
Figure 5:
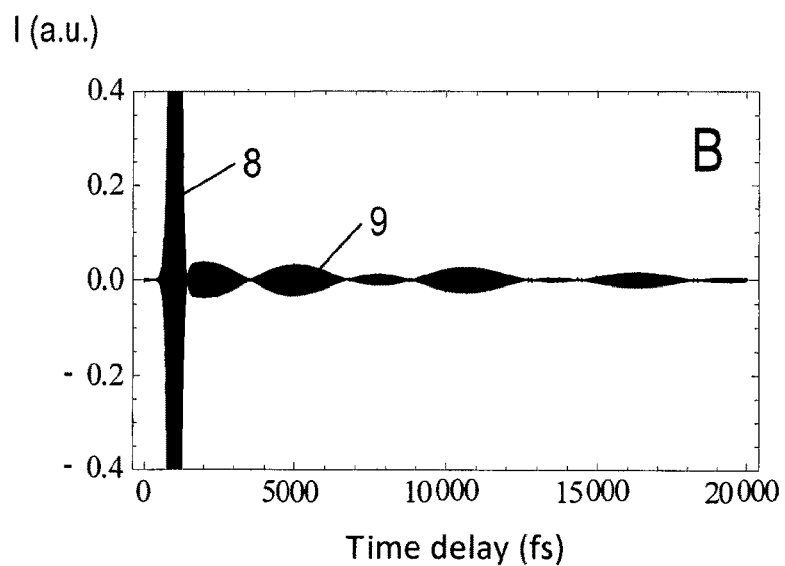

The Fourier transformation of the temporal shape, i. e. the Fourier transformation of the detector signal difference, yields the spectral response of the sample 1, as illustrated in FIGS. 4 and 5. Controlling the delay drive unit varying the mutual delay at the delay line 14, calibrating the detector signals of the detector elements 23, 24, collecting the detector signals, and calculating the Fourier transform can be done by a control unit, as it is known from conventional applications of the EOS method. The control unit can be provided as a separate circuitry (not shown) or as a section of the calculation unit 40 (see FIGS. 1, 2).

FIGS. 4 and 5 show examples of a frequency domain spectrum and a time domain signal obtained with the EOS method, resp. A modified spectrum of the probe light pulses 2' (MIR laser spectrum) in the frequency range of 500 to 2000 $cm^{-1}$ (wavelength range 20 μm to 5 μm) is displayed after passing an absorbing sample in FIG. 4. For demonstrating the principle, only two absorption lines 7 are shown. Electro-optical sampling then generates the field of the pulse in the time domain, which is essentially the Fourier Transform of the spectrum, as shown in FIG. 5A. It consists of a so-called centre-burst 8, corresponding to the broad primary spectrum of the probe light pulses, followed by a long tail 9 resulting from the narrow absorption lines 7. FIG. 5B shows the signal with the centre-burst 8 out of scale to show features of the tail 9. Advantageously, the inverse Fourier Transform of this signal is complex, including not only the power spectrum of the absorption lines 7 as in ordinary Fourier Transform spectroscopy, but the spectral phase as well. The pulse as shown is sampled over a time delay of 20 ps, which is equivalent to a spectral resolution of 1.7 $cm^{-1}$. The vertical scales of both diagrams are in arbitrary units.

FIG. 5 shows the background-free measurement according to the invention. As the temporal range is sampled after the end of the centre-burst, the detection is done with zero-background, i. e. without noise caused by the probe light pulses. This advantage cannot be obtained with broadband synchrotron radiation, which has pulse durations in the ps-range. Thus, the trails of spectral bands in the temporal shape would be superimposed by the synchrotron probe light.

After the Fourier transformation of the sampled temporal shape, the spectral response of the sample 1 can be further processed for obtaining diagnostically relevant information 6 (see FIGS. 1, 2). This further processing can be done by the calculation device 40. The spectral features of the absorption lines 7 can be obtained by subjecting the spectral response to a filtering process. Specific bands of compounds characteristic of the health status of a person can be identified. Furthermore, the spectral response can be compared with data previously collected with the same organism and/or with reference data collected with other, healthy or non-healthy subjects.

The features of the invention disclosed in the above description, the drawings and the claims can be of significance both individually as well as in combination or sub-combination for the realization of the invention in its various embodiments.

The invention claimed is:

1. A method of measuring a spectral response of a biological sample, comprising the steps:
   generation of probe light having a primary spectrum,
   irradiation of the sample with the probe light, including an interaction of the probe light and the sample, and
   spectrally resolved detection of the probe light having a modified spectrum, which deviates from the primary spectrum as a result of the interaction of the probe light and the sample, said modified spectrum being characteristic of the spectral response of the sample,
   wherein
   the probe light comprises probe light pulses being generated with a fs laser source device;
   the detection step comprises time-domain sampling a temporal shape of the probe light pulses after the intersection with the sample, and
   the spectral response of the sample is obtained based on a Fourier transformation of the temporal shape of the probe light pulses.

2. The method according to claim 1, wherein the probe light pulses have at least one of the features
   the probe light pulses have a pulse duration below a reciprocal frequency width of a spectrum including spectral response features occurring in the modified spectrum,
   the probe light pulses have a pulse duration below 50 fs before the irradiation of the sample,
   the probe light pulses have an average power above 50 mW before the irradiation of the sample,
   the primary spectrum covers at least one frequency octave,
   the primary spectrum covers a wavelength range including wavelengths of at least one of at least 5 μm and at most 15 μm, and
   the primary spectrum is a continuous or quasi-continuous spectrum.

3. The method according to claim 1, wherein
   the spectral response is at least one of an absorption spectrum and a reflection spectrum of the sample.

4. The method according to claim 1, having at least one of the features
   the sample comprises at least one of a solid, a liquid, an aerosol, a gas and a vapor, and
   the sample is arranged in a multipass cell or an enhancement cavity.

5. The method according to claim 1, wherein the fs laser source device includes
   a driving source creating driving pulses, and
   a difference frequency generation (DFG) unit generating the probe light pulses by intra-pulse frequency differences of the driving pulses.

6. The method according to claim 1, wherein the fs laser source device includes
   a fiber laser,
   an Yb-YAG disk laser, or
   a Ho-YAG disk laser.

7. The method according to claim 1, wherein
the time-domain sampling step comprises electro-optic sampling of the probe light pulses, wherein
the probe light pulses and sampling pulses are superimposed with varying temporal relationship in an electro-optic probe element for sampling the temporal shape of the probe light.

8. The method according to claim 7, wherein
the sampling pulses comprise parts of driving pulses used for the generation of the probe light pulses, said sampling pulses being directed to the electro-optic probe element with varying delay relative to the probe light pulses.

9. The method according to claim 1, comprising the further step
evaluation of the spectral response of the sample from a subject under investigation for obtaining diagnostically relevant information.

10. The method according to claim 9, wherein the evaluation step includes at least one of
identifying diagnostically relevant substances based on specific bands in the modified spectrum,
comparing at least a portion of the modified spectrum with a stored spectral response previously collected with another sample of the subject under investigation, and
comparing at least a portion of the modified spectrum with reference data of other subjects.

11. The method according to claim 1, wherein the probe light pulses have at least one of the features
the probe light pulses have a pulse duration below 20 fs before the irradiation of the sample,
the probe light pulses have an average power above 500 mW before the irradiation of the sample,
the primary spectrum covers at least two frequency octaves, and
the primary spectrum covers a wavelength range including wavelengths of at least one of at least 3 μm and at most 30 μm.

12. A spectroscopic measuring apparatus being configured for measuring a spectral response of a biological sample, comprising
a fs laser source device being arranged for an irradiation of the sample with probe light pulses having a primary spectrum, and
a detector device being arranged for a spectrally resolved detection of the probe light pulses after an interaction thereof with the sample, wherein;
the detector device is configured for the spectrally resolved detection of a modified spectrum deviating from the primary spectrum of the probe light pulses,
the detector device is configured for time-domain sampling a temporal shape of the probe light, and
the spectral response of the sample can be obtained based in a Fourier transformation of the temporal shape of the sample light.

13. The spectroscopic measuring apparatus according to claim 12, wherein the fs laser source device is configured for generating the probe light pulses with at least one of the features
the probe light pulses have a pulse duration below a reciprocal frequency width of a spectrum including spectral response features occurring in the modified spectrum,
the probe light pulses have a pulse duration below 50 fs, the probe light pulses have an average power above 50 mW,
the primary spectrum covers at least one frequency octave,
the primary spectrum covers a wavelength range including wavelengths of at least one of at least 5 μm and at most 15 μm, and
the primary spectrum is a continuous spectrum.

14. The spectroscopic measuring apparatus according to claim 12, further comprising at least one of
a sample holder device being arranged for accommodating the sample, wherein the fs laser source device, the sample holder device and the detector device are arranged relative to each other such that the detector device is capable of detecting at least one of absorption and reflection spectra of the sample, and
a multipass cell or an enhancement cavity being arranged for providing multiple passes of the probe light pulses through the sample.

15. The spectroscopic measuring apparatus according to claim 14, wherein
the sample holder device is configured for accommodating the sample as at least one of a solid, a liquid, an aerosol, a gas and a vapor.

16. The spectroscopic measuring apparatus according to claim 12, wherein the fs laser source device includes
a driving source creating driving pulses, and
a difference frequency generation (DFG) unit generating the probe light pulses by intra-pulse frequency differences of the driving pulses.

17. The spectroscopic measuring apparatus according to claim 12, wherein the fs laser source device includes
a fiber laser,
an Yb-YAG disk laser, or
a Ho-YAG disk laser.

18. The spectroscopic measuring apparatus according to claim 12, wherein
the detector device includes an electro-optic sampling unit with an electro-optic probe element for sampling the temporal shape of the probe light after the interaction with the sample.

19. The spectroscopic measuring apparatus according to claim 18, wherein
the fs laser source device includes a beam splitter for providing portions of driving pulses used for generating the probe light pulses as sampling pulses, and
a delay unit is arranged for providing the sampling pulses at the electro-optic probe element with varying delay relative to the probe light pulses.

20. The spectroscopic measuring apparatus according to claim 12, further including
a calculation device being configured for evaluating the spectral response of the sample from a subject under investigation and obtaining diagnostically relevant information.

21. The spectroscopic measuring apparatus according to claim 20, wherein the calculation device includes at least one of:
a filter unit identifying diagnostically relevant substances on the basis of specific bands in the modified spectrum,
a first comparing unit comparing at least a portion of the modified spectrum with a stored spectral response previously collected with another sample of the subject under investigation, and
a second comparing unit comparing at least a portion of the modified spectrum with reference data of other subjects.

22. The spectroscopic measuring apparatus according to claim 12, wherein the fs laser source device is configured for generating the probe light pulses with at least one of the features the probe light pulses have a pulse duration below 20 fs,
the probe light pulses have an average power above 500 mW,
the primary spectrum covers at least two frequency octaves, and
the primary spectrum covers a wavelength range including wavelengths of at least one of at least 3 µm and at most 30 µm.

* * * * *